United States Patent
Koh et al.

(10) Patent No.: US 10,886,564 B2
(45) Date of Patent: *Jan. 5, 2021

(54) ELECTROLYTE FOR LITHIUM SECONDARY BATTERY AND LITHIUM SECONDARY BATTERY INCLUDING THE ELECTROLYTE

(71) Applicants: Samsung Electronics Co., Ltd., Suwon-si (KR); Samsung SDI Co., Ltd., Yongin-si (KR)

(72) Inventors: Myongchun Koh, Hwaseong-si (KR); Hosang Park, Seoul (KR); Jinah Seo, Seoul (KR); Yoonsok Kang, Seongnam-si (KR)

(73) Assignees: SAMSUNG ELECTRONICS CO., LTD., Gyeonggi-do (KR); SAMSUNG SDI CO., LTD., Gyeonggi-do (KR)

( * ) Notice: Subject to any disclaimer, the term of this patent is extended or adjusted under 35 U.S.C. 154(b) by 276 days.

This patent is subject to a terminal disclaimer.

(21) Appl. No.: 15/631,968

(22) Filed: Jun. 23, 2017

(65) Prior Publication Data

US 2018/0065997 A1 Mar. 8, 2018

(30) Foreign Application Priority Data

Sep. 2, 2016 (KR) .................. 10-2016-0113259
May 29, 2017 (KR) .................. 10-2017-0066390

(51) Int. Cl.
| | |
|---|---|
| *H01M 10/0567* | (2010.01) |
| *H01M 4/485* | (2010.01) |
| *H01M 4/525* | (2010.01) |
| *H01M 10/052* | (2010.01) |
| *H01M 10/0568* | (2010.01) |
| *C07F 9/50* | (2006.01) |
| *C07F 9/6571* | (2006.01) |
| *H01M 10/056* | (2010.01) |
| *C07D 327/06* | (2006.01) |
| *C07F 1/02* | (2006.01) |

(52) U.S. Cl.
CPC ....... *H01M 10/0567* (2013.01); *C07F 9/5022* (2013.01); *C07F 9/6571* (2013.01); *H01M 4/485* (2013.01); *H01M 4/525* (2013.01); *H01M 10/052* (2013.01); *H01M 10/056* (2013.01); *H01M 10/0568* (2013.01); *C07D 327/06* (2013.01); *C07F 1/02* (2013.01); *H01M 2300/0025* (2013.01); *Y02T 10/70* (2013.01)

(58) Field of Classification Search
CPC ........ H01M 10/0567; H01M 10/0568; H01M 10/052; H01M 10/056; H01M 4/485; H01M 4/525; H01M 2300/0025; Y02T 10/70; C07F 9/5022; C07F 9/6571
See application file for complete search history.

(56) References Cited

U.S. PATENT DOCUMENTS

| | | | |
|---|---|---|---|
| 10,622,677 B2* | 4/2020 | Koh | .............. H01M 10/0567 |
| 2004/0091772 A1 | 5/2004 | Ravdel et al. | |
| 2010/0248039 A1 | 9/2010 | Oh et al. | |
| 2011/0151336 A1 | 6/2011 | Lee et al. | |
| 2014/0272607 A1 | 9/2014 | Amine et al. | |
| 2017/0317385 A1* | 11/2017 | Zhang | .............. H01M 10/0567 |
| 2018/0102570 A1* | 4/2018 | Koh | ..................... H01M 4/362 |

FOREIGN PATENT DOCUMENTS

| | | | |
|---|---|---|---|
| CN | 103441299 A | | 12/2013 |
| CN | 104218256 | * | 12/2014 |
| CN | 104218256 A | | 12/2014 |
| JP | 07153487 A | | 6/1995 |
| JP | 1995153487 A | | 6/1995 |
| JP | 2013062072 A | | 4/2013 |
| JP | 2014146518 A | | 8/2014 |

(Continued)

OTHER PUBLICATIONS

European Search Report for European Patent Application No. 17177007.6 dated Sep. 13, 2017.
Xu et al., "Tris (pentafluorophenyl) phosphine: An electrolyte additive for high voltage Li-ion batteries", Electrochemistry Communications, 18, 2012, 123-126.

*Primary Examiner* — Laura Weiner
(74) *Attorney, Agent, or Firm* — Cantor Colburn LLP

(57) ABSTRACT

An electrolyte for a lithium secondary battery, the electrolyte including: a compound represented by Formula 1; a lithium salt; and an organic solvent, wherein an amount of the compound represented by Formula 1 is less than about 3.0 weight percent, based on a total weight of the electrolyte:

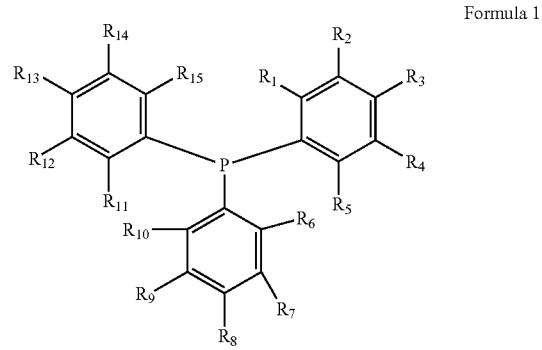

Formula 1 wherein, in Formula 1, $R_1$ to $R_{15}$ are each independently selected from hydrogen, fluorine, a C1-C10 alkyl group, and a C6-C10 aryl group.

18 Claims, 1 Drawing Sheet

(56) References Cited

FOREIGN PATENT DOCUMENTS

| KR | 1020090010373 | * | 1/2009 |
| KR | 1020090010373 A | | 1/2009 |
| KR | 1020150007145 A | | 1/2015 |
| KR | 1020150089712 A | | 8/2015 |
| WO | 2015153716 A1 | | 10/2015 |
| WO | 2016006381 A1 | | 1/2016 |

* cited by examiner

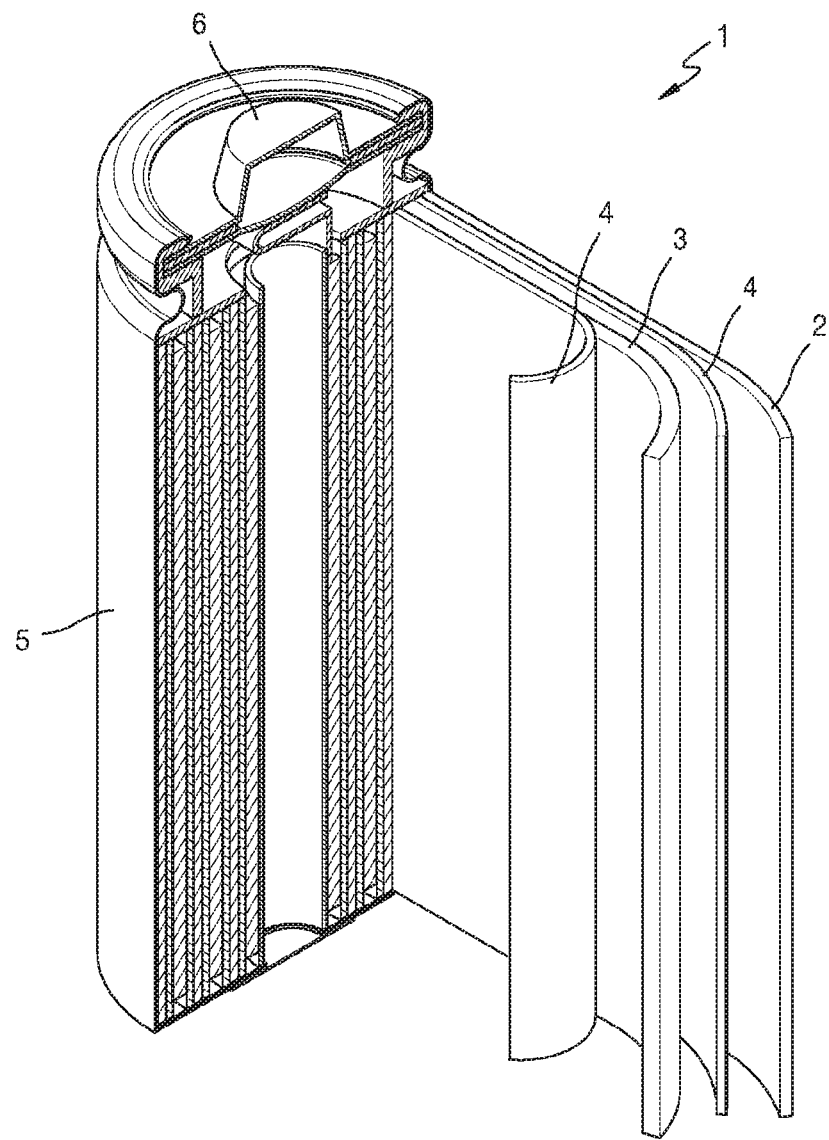

ELECTROLYTE FOR LITHIUM SECONDARY BATTERY AND LITHIUM SECONDARY BATTERY INCLUDING THE ELECTROLYTE

CROSS-REFERENCE TO RELATED APPLICATION

This application claims the benefit of and priority to Korean Patent Application Nos. 10-2016-0113259, filed on Sep. 2, 2016, and 10-2017-0066390, filed on May 29, 2017, in the Korean Intellectual Property Office, and all the benefits accruing therefrom under 35 U.S.C. § 119, the content of which is incorporated herein in its entirety by reference.

BACKGROUND

1. Field

The present disclosure relates to an electrolyte for a lithium secondary battery, and a lithium secondary battery including the electrolyte.

2. Description of the Related Art

As the electrical, electronics, telecommunications, and computer industries have rapidly developed, demand for secondary batteries having improved performance and improved safety have rapidly increased. In particular, along with the trends towards lighter, slimmer, and more compact electrical and electronic products with improved portability, there is a demand for lighter and smaller secondary batteries as core components of such products. Further, along with the concern over environmental pollution, such as air pollution and noise pollution from an increasing number of automobiles, and an increased demand for new energy sources to cope with the depletion of fossil fuels, there has been an increasing demand for electric vehicles to be developed as a solution to such problems, as well as batteries for electric vehicles which have improved power output and improved energy density. Recently, lithium secondary batteries have received significant attention as one of the new advanced high-performance next generation batteries to meet these current demands.

To manufacture a lithium secondary battery having high-density characteristics, nickel-rich positive active materials having high capacity characteristics may be used. However, such nickel-rich positive active materials have insufficient surface stability after battery operation, and so there is a need for improvement in this regard. Therefore, there is a continuing need for the development of an electrolyte that may improve the stability of positive active materials.

SUMMARY

Provided is an electrolyte for a lithium secondary battery having improved capacity and lifespan characteristics.

Provided is a lithium secondary battery including the electrolyte, the lithium secondary battery having improved cell performance due to the inclusion of the electrolyte.

Additional aspects will be set forth in part in the description which follows and, in part, will be apparent from the description, or may be learned by practice of the presented embodiments.

According to an aspect, an electrolyte for a lithium secondary battery includes:

a compound represented by Formula 1; a lithium salt; and an organic solvent, wherein an amount of the compound represented by Formula 1 is less than about 3.0 weight percent, based on a total weight of the electrolyte:

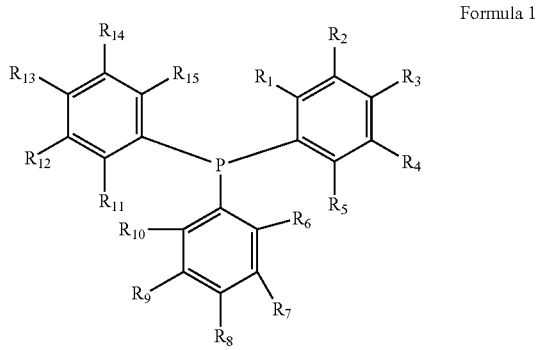

Formula 1 wherein, in Formula 1, $R_1$ to $R_{15}$ are each independently selected from hydrogen, fluorine, a substituted or unsubstituted C1-C10 alkyl group, and a substituted or unsubstituted C6-C10 aryl group.

The electrolyte includes at least one selected from vinylene carbonate, vinyl ethylene carbonate, maleic anhydride, and succinic anhydride.

According to an aspect, a lithium secondary battery includes:

a positive electrode;

a negative electrode; and at least one selected from the electrolyte and a reaction product of the electrolyte, disposed between the positive electrode and the negative electrode.

BRIEF DESCRIPTION OF THE DRAWINGS

These and/or other aspects will become apparent and more readily appreciated from the following description of the embodiments, taken in conjunction with the accompanying drawings in which:

FIG. 1 illustrates a structure of an embodiment of a lithium secondary battery.

DETAILED DESCRIPTION

Reference will now be made in detail to embodiments of an electrolyte for a lithium secondary battery and a lithium secondary battery including the electrolyte, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. "Or" means "and/or." Expressions such as "at least one of," when preceding a list of elements, modify the entire list of elements and do not modify the individual elements of the list.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that, although the terms "first," "second," "third," etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second element, component, region, layer, or section without departing from the teachings herein.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

It will be understood that when an element is referred to as being "on" another element, it can be directly on the other element or intervening elements may be present therebetween. In contrast, when an element is referred to as being "directly on" another element, there are no intervening elements present.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect of the present disclosure, an electrolyte for a lithium secondary battery includes: a compound represented by Formula 1; a lithium salt; and an organic solvent, wherein the amount of the compound represented by Formula 1 is less than about 3.0 weight percent (wt %), based on a total weight of the electrolyte. For example, the amount of the compound represented by Formula 1 may be about 0.1 wt % to about 2.9 wt %, and in an embodiment, about 0.1 wt % to about 2.4 wt %. The amount of the compound represented by Formula 1 may be, for example, about 0.5 wt % to about 2 wt %, based on the total weight of the electrolyte.

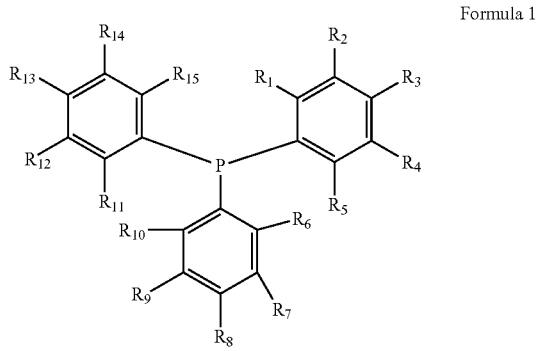

Formula 1

In Formula 1, $R_1$ to $R_{15}$ may each independently be selected from hydrogen, fluorine, a substituted or unsubstituted C1-C10 alkyl group, and a substituted or unsubstituted C6-C10 aryl group.

The electrolyte may further include at least one selected from vinylene carbonate, vinyl ethylene carbonate, maleic anhydride, and succinic anhydride.

When a nickel-rich lithium-nickel composite oxide is used as a positive active material for a lithium secondary battery, a lithium secondary battery having high power output and high capacity may be manufactured. However, a surface structure of the nickel-rich lithium-nickel composite oxide may become unstable after operation of the battery such that dissolution of a transition metal such as nickel may become severe. Accordingly, a lithium secondary battery using such a nickel-rich lithium-nickel composite oxide may have reduced high-temperature lifetime characteristics.

To address the above-described drawbacks, the inventors of the present disclosure provide an electrolyte that may effectively stabilize a surface of a nickel-rich lithium-nickel composite oxide.

The compound represented by Formula 1 may be a compound represented by Formula 2.

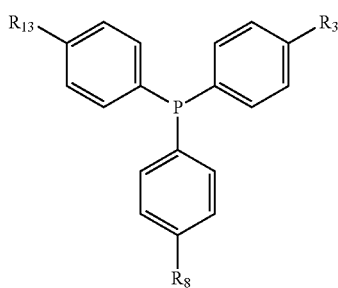

Formula 2

In Formula 2, $R_3$, $R_8$, and $R_{13}$ may each independently be selected from hydrogen, fluorine, and a methyl group. For example, $R_3$, $R_8$, and $R_{13}$ each may be fluorine, hydrogen, or a methyl group.

The compound of Formula 1 may have strong affinity to $Ni^{3+}$ on a surface of a positive electrode. Accordingly, the compound of Formula 1 may preferentially be adsorbed onto $Ni^{3+}$ on the surface of the positive electrode and thus protect $Ni^{3+}$ on the surface of the positive electrode. For example, the compound of Formula 1 may prevent complete dissolution of Ni from the surface of the positive electrode or minimize, for example prevent, surface destabilization of the positive electrode due to a valence change of Ni.

The compound represented by Formula 1 may be at least one selected from compounds represented by Formula 3, Formula 4, Formula 4, Formula 5, Formula 6, Formula 6a, and Formula 6b.

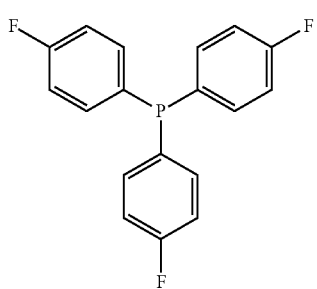

Formula 3

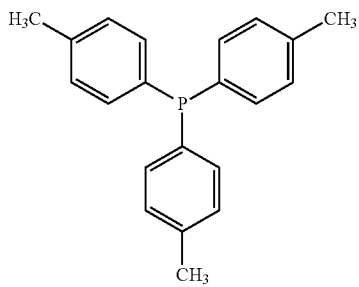

Formula 4

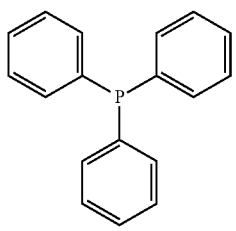

Formula 5

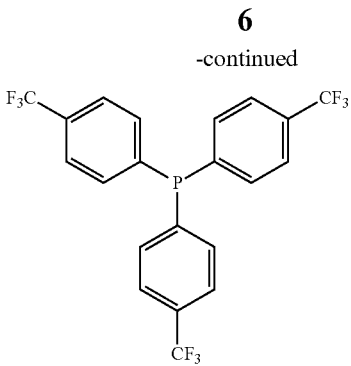

Formula 6

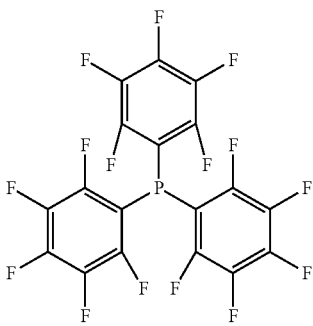

Formula 6a

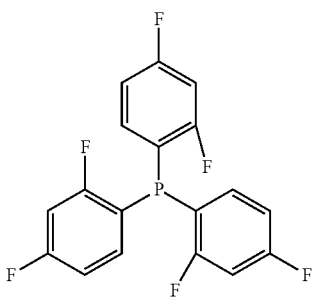

Formula 6b

The amount of the at least one selected from vinylene carbonate, vinyl ethylene carbonate, maleic anhydride, and succinic anhydride may be about 0.1 wt % to about 2 wt %, and in an embodiment, about 0.4 wt % to about 1.5 wt %, based on a total weight of the electrolyte. When the amount of the at least one selected from vinylene carbonate, vinyl ethylene carbonate, maleic anhydride, and succinic anhydride; is within these ranges, the electrolyte may improve lifetime characteristics of a lithium secondary battery and suppress resistance in the lithium secondary battery.

The electrolyte may include maleic anhydride, wherein the amount of the maleic anhydride may be about 0.1 wt % to about 2 wt %, and in an embodiment, about 0.4 wt % to about 1.5 wt %, based on a total weight of the electrolyte.

The electrolyte may further include fluoroethylene carbonate (FEC). The amount of FEC may be about 0.5 volume percent (volume %) to about 10 volume %, based on a total volume of the organic solvent. For example, the electrolyte may include about 0.5 volume % to about 8 volume % of FEC, and in an embodiment, about 1 volume % to about 7 volume % of FEC, based on a total volume of the organic solvent.

The organic solvent may comprise at least one selected from a carbonate-based solvent, an ester-based solvent, an ether-based solvent, and a ketone-based solvent.

Non-limiting examples of the carbonate-based solvent are dimethyl carbonate (DMC), diethyl carbonate (DEC), ethyl methyl carbonate (EMC), dipropyl carbonate (DPC), methylpropyl carbonate (MPC), ethylpropyl carbonate (EPC), ethylene carbonate (EC), propylene carbonate (PC), and butylene carbonate (BC). Non-limiting examples of the ether-based solvent are methyl acetate, ethyl acetate, n-propyl acetate, dimethyl acetate, methyl propionate (MP), ethyl propionate, γ-butyrolactone, decanolide, valerolactone, mevalonolactone, and caprolactone. Non-limiting examples of the ether-based solvent are dibutyl ether, tetraglyme, diglyme, dimethoxyethane, 2-methyltetrahydrofuran, and tetrahydrofuran. An example of the ketone-based solvent is cyclohexanone. The organic solvent may include, for example, tetraethylene glycol dimethyl ether (TEGDME).

In an embodiment, the organic solvent may include, for example, about 50 volume % to about 95 volume % of a chain carbonate and about 5 volume % to about 50 volume % of a cyclic carbonate, based on the total volume of the organic solvent.

The chain carbonate may be at least one selected from ethyl methyl carbonate (EMC), methyl propyl carbonate, ethyl propyl carbonate, dimethyl carbonate (DMC), diethyl carbonate (DEC), and dipropyl carbonate. The cyclic carbonate may be at least one selected from ethylene carbonate, propylene carbonate, and butylene carbonate.

In an embodiment, the electrolyte may stabilize a surface of a nickel-rich lithium-nickel composite oxide. This surface stabilization effect of the electrolyte may be identified from the amount of Ni dissolved from the positive electrode including the nickel-rich lithium-nickel composite oxide after high-temperature storage or high-temperature cycles. In particular, when an electrolyte according to an embodiment is used, Ni in the surface of a positive electrode may be stabilized so that the amount of Ni dissolved into the electrolyte after high-temperature storage or high-temperature cycles may be reduced, compared to when not using an electrolyte according to an embodiment.

When using an electrolyte according to an embodiment having the above-described features, a lithium secondary battery may have improved high-temperature lifetime characteristics and improved resistance suppression.

The electrolyte may include a disultone compound represented by Formula 7.

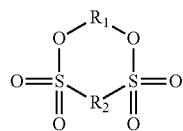

Formula 7

In Formula 7, $R_1$ and $R_2$ may each independently be selected from a substituted or unsubstituted C1-C30 alkylene group, and a substituent of the substituted C1-C30 alkylene group may be selected from a halogen, a methyl group, an ethyl group, a propyl group, an isopropyl group, an n-butyl group, a sec-butyl group, a tert-butyl group, a vinyl group, a propinyl group, a butynyl group, a propenyl group, and a butenyl group.

The disultone compound may be, for example, a disultone compound represented by Formula 7a.

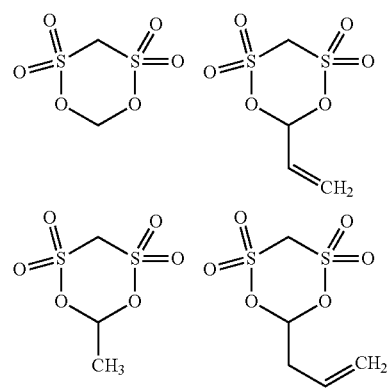

Formula 7a

The amount of the disultone compound represented by Formula 7a may be about 0.1 wt % to about 5 wt %, based on a total weight of the electrolyte. When the amount of the disultone compound is within this range, a lithium secondary battery including the electrolyte may have improved lifetime characteristics.

The disultone compound may be, for example, a compound represented by Formula 15.

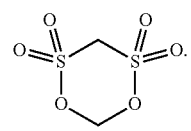

Formula 15

The disultone compound may have a cyclic structure including two sulfonyl groups. When such a disultone compound is added to an electrolyte, the electrolyte may have high-temperature stability due to the two included sulfonyl groups. The disultone compound may be reduced and decomposed earlier than the other components of electrolyte due to having the cyclic structure, thus forming a sulfonate (—$SO_3$—)-based polymer film. This polymer film may cover an increased area of an electrode, and moreover, such a sulfonate (—$SO_3$—)-based polymer film may have improved high-temperature stability. Thus, the electrolyte may have an enhanced resistance suppression effect at high temperatures.

In an embodiment, a concentration of the lithium salt in the electrolyte may be about 0.1 moles per liter (molar, M) to about 5.0 M, for example, about 0.1 M to about 2.0 M. For example, a concentration of the lithium salt in the electrolyte may be about 1 M to 2 M. However, the concentration of the lithium salt is not limited to these ranges, and the concentration of the lithium salt may be varied appropriately, if needed. When the concentration of the lithium salt is within these ranges, improved battery characteristics may be obtained.

The lithium salt may be at least one selected from $LiPF_6$, $LiBF_4$, $LiCF_3SO_3$, $Li(CF_3SO_2)_2N$, $LiC_4F_9SO_3$, [Li($FSO_2$)$_2$N], $LiN(SO_2CF_2CF_3)_2$, and a compound represented by Formula 8 to Formula 11.

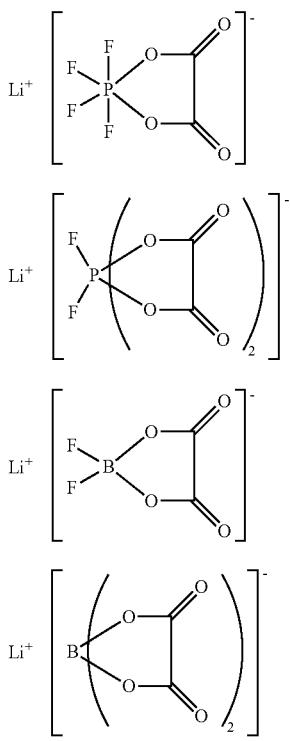

Formula 8

Formula 9

Formula 10

Formula 11

In an embodiment, the lithium salt of the electrolyte may be, for example, at least one selected from lithium difluoro (oxalate)borate (LiDFOB) represented by Formula 11 and LiPF$_6$.

According to another aspect of the present disclosure, a lithium secondary battery includes a positive electrode as described above, a negative electrode, and at least one selected from an electrolyte according to one of the above-described embodiments and a reaction product of the electrolyte with at least one selected from the positive electrode and the negative electrode.

As used herein, the term "reaction product of an electrolyte" refers to a product of reaction of the electrolyte with itself during or after operation of the lithium secondary battery, or a product of reaction of the electrolyte with other components of the battery.

The positive electrode may include a nickel-rich lithium-nickel composite oxide containing about 70 mol % to about 95 mol % of nickel, for example, about 80 mol % to about 93 mol % of nickel, with respect to a total molar amount of transition metals in the nickel-rich lithium-nickel composite oxide.

The nickel-rich lithium-nickel composite oxide may be, for example, a compound represented by Formula 14.

$$Li_aNi_xCo_yMn_zM_cO_{2-b}A_b$$   Formula 14

In Formula 14, 1.0≤a≤1.2, 0.7≤x<1, 0<y<1, 0≤z<1, 0≤c<1, x+y+z+c=1, 0≤b≤0.2, M may be at least one selected from vanadium (V), magnesium (Mg), gallium (Ga), silicon (Si), tungsten (W), molybdenum (Mo), iron (Fe), chromium (Cr), copper (Cu), zinc (Zn), titanium (Ti), aluminum (Al), and boron (B), and A may be at least one selected from F, S, Cl, and Br.

The compound of Formula 14 of the positive electrode may be, for example, at least one compound represented by Formula 14a and Formula 14b.

$$LiNi_xCo_yMn_zO_2$$   Formula 14a $$LiNi_xCo_yAl_zO_2$$   Formula 14b

In Formulae 14a and 14b, 0.8≤x≤0.95, 0<y≤0.2, and 0<z≤0.1.

Non-limiting examples of the nickel-rich lithium-nickel composite oxide include $LiNi_{0.7}Co_{0.2}Mn_{0.1}O_2$, $LiNi_{0.8}Co_{0.15}Mn_{0.05}O_2$, $LiNi_{0.8}Co_{0.1}Mn_{0.1}O_2$, $LiNi_{0.68}Co_{0.1}Mn_{0.02}O_2$, $LiNi_{0.8}Co_{0.15}Al_{0.05}O_2$, $LiNi_{0.8}Co_{0.1}Mn_{0.2}O_2$, and $LiNi_{0.88}Co_{0.1}Al_{0.02}O_2$.

The negative electrode may include at least one selected from a silicon compound, a carbonaceous material, a composite of a silicon-based compound and a carbonaceous material, and a silicon oxide of the formula SiO$_x$, wherein 0<x<2. The carbonaceous material may, for example, include graphite.

The lithium secondary battery including an electrolyte according to any of the above-described embodiments may have a direct current internal resistance (DCIR) after 300 cycles of charging and discharging that is about 165% or less, for example, about 105% to about 150%, of a direct current internal resistance of the lithium secondary battery after 1 cycle of charging and discharging, as measured at about 45° C.

In an embodiment, the electrolyte may include: i) at least one selected from tri(4-fluorophenyl)phosphine, triphenylphosphine, tri(4-methylphenyl) phosphine, tris(2,4-difluorophenyl)phosphine, and tris(pentafluorophenyl)phosphine; and ethylene carbonate, fluoroethylene carbonate, ethyl methyl carbonate, dimethyl carbonate, and vinylene carbonate, or ii) at least one selected from tri(4-fluorophenyl)phosphine, triphenylphosphine, tri(4-methylphenyl) phosphine, tris(2,4-difluorophenyl)phosphine, and tris(pentafluorophenyl)phosphine; and ethylene carbonate, ethyl methyl carbonate, dimethyl carbonate, and vinylene carbonate.

For example, the electrolyte may include at least one selected from tri(4-fluorophenyl)phosphine, triphenylphosphine, and tri(4-methylphenyl) phosphine; and ethylene carbonate, fluoroethylene carbonate, ethyl methyl carbonate, dimethyl carbonate, and vinylene carbonate. The amount of the tri(4-fluorophenyl)phosphine may be about 0.5 wt % to about 1.5 wt %, based on a total weight of the electrolyte; a volume ratio of the ethylene carbonate, the fluoroethylene carbonate, the ethyl methyl carbonate, and the dimethyl carbonate may be about 7:7:46:40; and the amount of vinylene carbonate may be about 0.5 wt % to about 1.5 wt %, based on the total weight of the electrolyte.

As another example, the electrolyte may include at least one selected from tri(4-fluorophenyl)phosphine, triphenylphosphine, and tri(4-methylphenyl) phosphine; and ethylene carbonate, ethyl methyl carbonate, dimethyl carbonate, and vinylene carbonate. The amount of the tri(4-fluorophenyl)phosphine may be about 0.5 wt % to about 1.5 wt %, based on the total weight of the electrolyte; a volume ratio of ethylene carbonate, ethyl methyl carbonate, and dimethyl carbonate may be about 20:40:40; and the amount of vinylene carbonate may be about 0.5 wt % to about 1.5 wt %, based on the total weight of the electrolyte.

In an embodiment, a volume ratio of the ethylene carbonate, the ethyl methyl carbonate, and the dimethyl carbonate may be about 20:40:40.

In an embodiment, a volume ratio of the ethylene carbonate, the fluoroethylene carbonate, the ethyl methyl carbonate, and the dimethyl carbonate may be about 17:3:40:40.

The shape and type of the lithium secondary battery are not specifically limited. For example, types of the lithium secondary battery may include a lithium ion battery, a lithium ion polymer battery, and a lithium sulfur battery.

A lithium secondary battery according to an example embodiment may be manufactured as follows.

First, a positive electrode may be prepared as follows.

For example, a positive active material, a conducting agent, a binder, and a solvent may be mixed together to prepare a positive active material composition. The positive active material composition may be directly coated on a positive electrode current collector to prepare a positive electrode. In another embodiment, the positive active material composition may be cast on a separate support to form a positive active material film. The positive active material film may then be separated from the support and laminated on a positive electrode current collector, to thereby prepare the positive electrode. In an embodiment, the positive electrode may be any of a variety of types, and is not limited to these examples.

In an embodiment, the positive active material may further include a common lithium-containing metal oxide, in addition to a nickel-rich lithium-nickel composite oxide as described above. For example, the lithium-containing metal oxide may be at least one selected from a composite oxide of lithium with cobalt, a composite oxide of lithium with manganese, a composite oxide of lithium with nickel, and a composite oxide of lithium with a combination of at least two selected from cobalt, manganese, and nickel. For example, the lithium-containing metal oxide may be a compound represented by one of the following formulae: $Li_aA_{1-b}B'_bD_2$ (wherein $0.90 \leq a \leq 1.8$ and $0 \leq b \leq 0.5$); $Li_aE_{1-b}B'_bO_{2-c}D_c$ (wherein $0.90 \leq a \leq 1.8$, $0 \leq b \leq 0.5$, and $0 \leq c \leq 0.05$); $LiE_{2-b}B'_bO_{4-c}D_c$ (wherein $0 \leq b \leq 0.5$ and, $0 \leq c \leq 0.05$); $Li_aNi_{1-b-c}Co_bB'_cD_\alpha$ (wherein $0.90 \leq a \leq 1.8$, $0 \leq b \leq 0.5$, $0 \leq c \leq 0.05$, and $0 < \alpha \leq 2$); $Li_aNi_{1-b-c}Co_bB'_cO_{2-\alpha}F'_\alpha$ (wherein $0.90 \leq a \leq 1.8$, $0 \leq b \leq 0.5$, $0 \leq c \leq 0.05$, and $0 < \alpha < 2$); $Li_aNi_{1-b-c}Co_bB'_cO_{2-\alpha}F'_2$ (wherein $0.90 \leq a \leq 1.8$, $0 \leq b \leq 0.5$, $0 \leq c \leq 0.05$, and $0 < \alpha < 2$); $Li_aNi_{1-b-c}Mn_bB'_cD_\alpha$ (wherein $0.90 \leq a \leq 1.8$, $0 \leq b \leq 0.5$, $0 \leq c \leq 0.05$, and $0 < \alpha \leq 2$); $Li_aNi_{1-b-c}Mn_bB'_cO_{2-\alpha}F'_\alpha$ (wherein $0.90 \leq a \leq 1.8$, $0 \leq b \leq 0.5$, $0 \leq c \leq 0.05$, and $0 < \alpha < 2$); $Li_aNi_{1-b-c}Mn_bB'_cO_{2-\alpha}F'_2$ (wherein $0.90 \leq a \leq 1.8$, $0 \leq b \leq 0.5$, $0 \leq c \leq 0.05$, and $0 < \alpha < 2$); $Li_aNi_bE_cG_dO_2$ (wherein $0.90 \leq a \leq 1.8$, $0 \leq b \leq 0.9$, $0 \leq c \leq 0.5$, and $0.001 \leq d \leq 0.1$); $Li_aNi_bCo_cMn_dGeO_2$ (wherein $0.90 \leq a \leq 1.8$, $0 \leq b \leq 0.9$, $0 \leq c \leq 0.5$, $0 \leq d \leq 0.5$, and $0.001 \leq e \leq 0.1$); $Li_aNiG_bO_2$ (wherein $0.90 \leq a \leq 1.8$ and $0.001 \leq b \leq 0.1$); $Li_aCoG_bO_2$ (wherein $0.90 \leq a \leq 1.8$ and $0.001 \leq b \leq 0.1$); $Li_aMnG_bO_2$ (wherein $0.90 \leq a \leq 1.8$ and $0.001 \leq b \leq 0.1$); $Li_aMn_2G_bO_4$ (wherein $0.90 \leq a \leq 1.8$ and $0.001 \leq b \leq 0.1$); $LiQS_2$; $LiV_2O_5$; $LiI'O_2$; $LiNiVO_4$; $Li_{(3-f)}J_2(PO_4)_3$ (wherein $0 \leq f \leq 2$); $Li_{(3-f)}Fe_2(PO_4)_3$ (wherein $0 \leq f \leq 2$); and $LiFePO_4$.

In an embodiment, the positive active material may further include $V_2O_5$.

In the above formulae, A may be at least one selected from nickel (Ni), cobalt (Co), and manganese (Mn); B' may be at least one selected from aluminum (Al), nickel (Ni), cobalt (Co), manganese (Mn), chromium (Cr), iron (Fe), magnesium (Mg), strontium (Sr), vanadium (V), and a rare earth element; D may be at least one selected from oxygen (O), fluorine (F), sulfur (S), and phosphorus (P); F' may be at least one selected from fluorine (F), sulfur (S), and phosphorus (P); G may be at least one selected from aluminum (Al), chromium (Cr), manganese (Mn), iron (Fe), magnesium (Mg), lanthanum (La), cerium (Ce), strontium (Sr), and vanadium (V); Q may be at least one selected from titanium (Ti), molybdenum (Mo), and manganese (Mn); I' may be at least one selected from chromium (Cr), vanadium (V), iron (Fe), scandium (Sc), and yttrium (Y); and J may be at least one selected from vanadium (V), chromium (Cr), manganese (Mn), cobalt (Co), nickel (Ni), and copper (Cu).

For example, the lithium-containing metal oxide may be at least one selected from $LiCoO_2$, $LiMn_xO_{2x}$ (wherein $x=1$ or 2), $LiNi_{1-x}Mn_xO_{2x}$ (wherein $0 < x < 1$), $LiNi_{1-x-y}Co_xMn_yO_2$ (wherein $0 \leq x \leq 0.5$, $0 \leq y \leq 0.5$, and $1-x-y > 0.5$), and $LiFePO_4$.

The compounds listed above as the lithium-containing metal oxide may have a surface coating layer (hereinafter, also referred to as "coating layer"). Alternatively, a mixture of a compound without a coating layer and a compound having a coating layer, the compounds being selected from the compounds listed above, may be used. In an embodiment, the coating layer may include at least one compound selected from oxide, hydroxide, oxyhydroxide, oxycarbonate, and hydroxyl carbonate as a coating element. In an embodiment, the compounds for forming the coating layer may be amorphous or crystalline. In an embodiment, the coating element for forming the coating layer may be at least one selected from magnesium (Mg), aluminum (Al), cobalt (Co), potassium (K), sodium (Na), calcium (Ca), silicon (Si), titanium (Ti), vanadium (V), tin (Sn), germanium (Ge), gallium (Ga), boron (B), arsenic (As), and zirconium (Zr). In an embodiment, the coating layer may be formed using any suitable method that does not adversely affect the physical characteristics of the positive active material when the coating element compound is used. For example, the coating layer may be formed using spray coating or dipping. These coating methods will be obvious to one of ordinary skill in the art, and thus a detailed description thereof will be omitted The conducting agent may be any suitable material having conductivity that does not cause a chemical change in the lithium secondary battery. Non-limiting examples of the conducting agent include graphite such as natural graphite or artificial graphite; carbon black, acetylene black, Ketjen black, channel black, furnace black, lamp black, or summer black; conductive fibers, such as carbon fibers or metal fibers; carbon fluoride; metal powder, such as aluminum or nickel powder; conductive whiskers, such as zinc oxide or potassium titanate; a conductive metal oxide, such as a titanium oxide; and a conductive polymer, such as a polyphenylene derivative.

The amount of the conducting agent may be about 1 wt % to about 20 wt %, based on a total weight of the positive active material composition.

The binder may facilitate binding between the positive active material and the conducting agent, and binding of the positive active material composition to the current collector. For example, the amount of the binder may be about 1 wt % to about 30 wt %, based on a total weight of the positive active material composition. Non-limiting examples of the binder include polyvinylidene fluoride (PVDF), polyvinylidene chloride, polybenzimidazole, polyimide, polyvinyl acetate, polyacrylonitrile, polyvinyl alcohol, carboxymethyl cellulose (CMC), starch, hydroxypropyl cellulose, regenerated cellulose, polyvinylpyrrolidone, polyethylene, polypropylene, polystyrene, polymethyl methacrylate, polyaniline, acrylonitrile butadiene styrene, phenol resin, epoxy resin, polyethylene terephthalate, polytetrafluoroethylene, polyphenylene sulfide, polyamide imide, polyether imide, polyether sulfone, polyamide, polyacetal, polyphenylene oxide, polybutylene terephthalate, ethylene-propylene-diene monomer (EPDM), sulfonated EPDM, styrene-butadiene rubber (SBR), fluoro rubber, and various suitable copolymers.

The solvent may be, for example, N-methylpyrrolidone (NMP), acetone, or water. However, examples of the solvent are not limited thereto. Any suitable solvent, including those available in the art, may be used. The amount of the solvent may be about 10 parts to about 100 parts by weight, based on 100 parts by weight of the positive active material. When the amount of the solvent is within this range, the positive active material film may be formed.

The amounts of the positive active material, the conducting agent, the binder, and the solvent may be the same as amounts used in lithium secondary batteries. At least one of the conducting agent, the binder, and the solvent may be omitted depending on the use and structure of the lithium secondary battery.

For example, N-methylpyrrolidone (NMP) may be used as the solvent, PVdF or a PVdF copolymer may be used as the binder, and carbon black or acetylene black may be used as the conducting agent. For example, after about 94 wt % of the positive active material, about 3 wt % of the binder, and about 3 wt % of the conducting agent are mixed together to obtain a mixture in power form, NMP may be added to the mixture to prepare a slurry having a solid content of about 70 wt %. This slurry is then coated, dried, and roll-pressed, to thereby manufacture a positive electrode.

The positive electrode current collector may have a thickness of about 3 micrometers ($\mu$m) to about 50 $\mu$m. The positive electrode current collector is not particularly limited, and may be any suitable material having a high conductivity without causing chemical changes in the fabricated battery. For example, the positive electrode current collector may be at least one selected from a stainless steel, aluminum, nickel, titanium, sintered carbon, aluminum, and a stainless steel that is surface-treated with carbon, nickel, titanium, or silver. For example, the positive electrode current collector may be processed to have an uneven surface with fine projections and recesses to enhance the adhesion of the positive active material to the surface of the positive electrode current collector. The positive electrode current collector may be of various forms, including a film, a sheet, a foil, a net, a porous structure, a foam, and a non-woven fabric.

A loading level of the prepared positive active material composition may be about 30 milligrams per square centimeter (mg/cm$^2$) or greater, and in an embodiment, about 35 mg/cm$^2$ or greater, and in another embodiment, about 40 mg/cm$^2$ or greater. An electrode density of the positive electrode may be about 3 grams per cubic centimeter (g/cc) or greater, and in an embodiment, about 3.5 g/cc or greater. For an energy density-oriented design, the positive electrode may have a loading level of about 35 mg/cm$^2$ to about 50 mg/cm$^2$, and a density of about 3.5 g/cc to about 4.2 g/cc. For example, the positive electrode current collector may use a double-side coated electrode plate having a loading level of about 37 mg/cm$^2$ and a density of about 3.6 g/cc.

When a loading level of the positive active material composition and a positive electrode density are within the above ranges, a lithium secondary battery including such a positive active electrode may exhibit a high cell energy density of about 500 watt hours per liter (Wh/L) or greater. The lithium secondary battery may have a direct current internal resistance (DCIR) after 300 cycles of charging and discharging that is about 165% or less of a direct current internal resistance of the lithium secondary battery after 1 cycle of charging and discharging at about 45° C.

Next, a negative electrode may be prepared as follows.

For example, a negative active material, a conducting agent, a binder, and a solvent may be mixed together to prepare a negative active material composition. The negative active material composition may be directly coated on a negative electrode current collector and then dried to prepare a negative electrode. In another embodiment, the negative active material composition may be cast on a separate support to form a negative active material film. The negative active material film may then be separated from the support and laminated on a metallic negative electrode current collector, to thereby prepare a negative electrode.

The negative active material may be, for example, at least one selected from a silicon-based compound, a carbonaceous material, a silicon oxide (SiO$_x$, wherein 0<x<2), and a composite of a silicon-based compound and a carbonaceous material. The silicon particles of the negative active material may have a size (for example, an average particle diameter) of less than about 200 nanometers (nm), for example, about 10 nm to about 150 nm. The term "size" or "particle size" may refer to an average particle diameter when the silicon particles are spherical or refer to an average length of the major axes of particles when the silicon particles are nonspherical.

When the size of the silicon particles is within the above ranges, a lithium secondary battery may have improved lifetime characteristics. Accordingly, when the lithium secondary battery uses an electrolyte according to one of the embodiments and includes the silicon particles having such a size, the lithium secondary battery may have further improved lifetime characteristics.

The carbonaceous material may be crystalline carbon, amorphous carbon, or a mixture thereof. The crystalline carbon may be graphite, such as natural graphite or artificial graphite, in non-shaped, plate, flake, spherical, or fibrous form. For example, the amorphous carbon may be soft carbon (carbon sintered at low temperatures), hard carbon, meso-phase pitch carbonization products, sintered corks, and the like.

For example, the composite of a silicon-based compound and a carbonaceous material may be a composite including silicon particles on graphite, or a composite including silicon particles on and inside graphite. The composite of a silicon-based compound and a carbonaceous material may be an active material prepared by dispersing Si particles having an average particle diameter of about 200 nm or less, and in an embodiment, about 100 nm to about 200 nm, and in another embodiment, about 150 nm, on graphite particles, and carbon-coating the resulting particles or an active material including the Si particles on and inside graphite. These composites are commercially available under the product name "SCN1" (Si particles on graphite) or "SCN2" (Si particles inside as well as on graphite). SCN1 is an active material obtained by dispersing Si particles having an average particle diameter of about 150 nm on graphite particles and carbon-coating the resulting particles. SCN2 is an active material including Si particles having an average particle diameter of about 150 nm on and inside graphite.

The negative active material of the negative electrode may further include any suitable material available as a negative active material of a lithium secondary battery, including those available in the art, which may be used together with the above-described negative active materials. For example, materials that may be used together with the above-described negative active materials may be Si, Sn, Al, Ge, Pb, Bi, Sb, a Si—Y' alloy (wherein Y' may be an alkaline metal, an alkaline earth metal, a Group 13 to Group 16 element, a transition metal, a rare earth element, or a combination thereof, but may not be Si), and a Sn—Y' alloy (wherein Y' may be an alkaline metal, an alkaline earth metal, a Group 13 to Group 16 element, a transition metal, a rare earth element, or a combination thereof, but may not be Sn). The element Y' may be magnesium (Mg), calcium (Ca), strontium (Sr), barium (Ba), radium (Ra), scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), technetium (Tc), rhenium (Re), bohrium (Bh), iron (Fe), lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), aluminum (Al), gallium (Ga), tin (Sn), indium (In), thallium (Tl), germanium (Ge), phosphorus (P), arsenic (As), antimony (Sb), bismuth (Bi), sulfur (S), selenium (Se), tellurium (Te), polonium (Po), or a combination thereof.

For example, the negative active material may be a lithium titanium oxide, a vanadium oxide, a lithium vanadium oxide, and the like.

The conducting agent and the binder used in the negative active material composition may be the same as those used in the positive active material composition.

The negative active material composition may use water as a solvent, unlike the positive active material composition. For example, the negative active material composition may include water as a solvent; carboxymethyl cellulose (CMC), styrene-butadiene rubber (SBR), an acrylate polymer, or a methacrylate polymer as a binder; and carbon black, acetylene black, or graphite as a conducting agent.

The amounts of the negative active material, the conducting agent, the binder, and the solvent may be the same as amounts used in lithium secondary batteries. At least one of the conducting agent, the binder, and the solvent may be omitted depending on the use and structure of the lithium secondary battery.

For example, after about 94 wt % of the negative active material, about 3 wt % of the binder, and about 3 wt % of the conducting agent are mixed together to obtain a mixture in powder form, water may be added to the mixture to prepare a slurry having a solid content of about 70 wt %. This slurry is then coated, dried, and roll-pressed to thereby manufacture a negative electrode.

The negative electrode current collector may have a thickness of about 3 µm to about 50 µm. The negative electrode current collector is not particularly limited, and may be a material having suitable conductivity without causing chemical changes in the fabricated battery. For example, the negative electrode current collector may be copper; a stainless steel; aluminum; nickel; titanium; sintered carbon; copper or a stainless steel that is surface-treated with carbon, nickel, titanium, or silver; and an aluminum-cadmium alloy. Similar to the positive electrode current collector, the negative electrode current collector may be processed to have an uneven surface with fine projections and recesses to enhance the adhesion of the negative active material to the surface of the negative electrode current collector. The negative electrode current collector may be of various forms, including a film, a sheet, a foil, a net, a porous structure, a foam, and a non-woven fabric.

A loading level of the negative active material composition may be determined by the loading level of the positive active material composition. For example, a loading level of the negative active material composition may be about 12 mg/cm$^2$ or greater, and in an embodiment, about 15 mg/cm$^2$ or greater, depending on the capacity per gram of the negative active material composition. An electrode density of the negative electrode current collector may be about 1.5 g/cc or greater, and in an embodiment, about 1.6 g/cc or greater. For an energy density-oriented design, the negative electrode may have a density of about 1.65 g/cc to about 1.9 g/cc.

When a loading level of the negative active material composition and a negative electrode density are within the above ranges, a lithium secondary battery including such a negative electrode may exhibit a high cell energy density of about 500 Wh/l or greater.

Next, a separator that may be disposed between the positive electrode and the negative electrode is prepared.

The separator may be any suitable separator used in lithium batteries. A suitable separator may have low resistance to migration of ions in an electrolyte, and a good electrolyte-retaining ability. For example, a material of the separator may be at least one selected from glass fiber, polyester, Teflon, polyethylene, polypropylene, and polytetrafluoroethylene (PTFE), each of which may be a nonwoven fabric or a woven fabric. For example, a rollable separator including polyethylene or polypropylene may be used in a lithium ion battery. A separator with a good electrolyte-retaining ability may be used in a lithium ion polymer battery. For example, the separator may be manufactured as follows.

In an embodiment, a polymer resin, a filler, and a solvent may be mixed together to prepare a separator composition. Then, the separator composition may be directly coated on an electrode and dried to form the separator. In an embodiment, the separator composition may be cast on a support and dried to form a separator film. The separator film may then be separated from the support and laminated on an electrode to form the separator.

The polymer resin that may be used to manufacture the separator may be any suitable material used as a binder for electrode plates. For example, the polymer resin may be at least one selected from a vinylidenefluoride/hexafluoropropylene copolymer, polyvinylidene fluoride (PVDF), polyacrylonitrile, and polymethylmethacrylate.

Next, the electrolyte is prepared.

In an embodiment, the electrolyte may include a non-aqueous electrolyte solution, an organic solid electrolyte, or an inorganic solid electrolyte.

The organic solid electrolyte may be, for example, at least one selected from a polyethylene derivative, a polyethylene oxide derivative, a polypropylene oxide derivative, a phosphoric acid ester polymer, polyester sulfide, polyvinyl alcohol, polyfluoride vinylidene, and a polymer including ionic dissociative groups.

The inorganic solid electrolyte may be at least one selected from $Li_3N$, $LiI$, $Li_5NI_2$, $Li_3N$—$LiI$—$LiOH$, $Li_2SiS_3$, $Li_4SiO_4$, $Li_4SiO_4$—$LiI$—$LiOH$, and $Li_3PO_4$—$Li_2S$—$SiS_2$.

Referring to FIG. 1, a lithium secondary battery 1 according to an example embodiment includes a positive electrode 3, a negative electrode 2, and a separator 4. The positive electrode 3, the negative electrode 2, and the separator 4 may be wound or folded, and then sealed in a battery case 5. Subsequently, an electrolyte may be injected into the battery case 5, and the battery case 5 may then be sealed with a cap assembly 6, to thereby complete the manufacture of the lithium secondary battery 1. For example, the battery case 5 may be a cylindrical type, a rectangular type, or a thin-film type. For example, the lithium secondary battery 1 may be a large thin-film type battery. In an embodiment, the lithium secondary battery 1 may be a lithium ion battery.

In an embodiment, the positive electrode 3, the negative electrode 2, and the separator 4 between the positive electrode 3 and the negative electrode 2 may form a battery assembly. The battery assembly may be stacked in a bi-cell structure and impregnated with the electrolyte. The resultant assembly may be put into a pouch and hermetically sealed, to thereby complete the manufacture of a lithium ion polymer battery.

In an embodiment, a plurality of battery assemblies may be stacked to form a battery pack. The battery pack may be used in any device that requires high capacity and high output, for example, in a laptop computer, a smartphone, or an electric vehicle.

A lithium secondary battery according to one of the above-described embodiments may have a remarkably reduced increase in DCIR after 300 cycles of charging and discharging and improved battery characteristics as compared with a lithium secondary battery using a common nickel-rich lithium-nickel composite oxide as a positive active material.

A lithium secondary battery according to an embodiment employing a positive electrode, a negative electrode, and an electrolyte as described above may have an operating voltage of, for example, about 2.5-2.8 volts (V) as a lower limit to about 4.1-4.4 V as an upper limit, and an energy density of, for example, about 500 Wh/l or greater.

A lithium secondary battery according to one of the above-described embodiments may be used in, for example, power tools actuated by electric motors; electric vehicles (EVs), including hybrid electric vehicles (HEVs), plug-in hybrid electric vehicles (PHEV), and the like; electric two-wheeled vehicles, including electric bicycles and electric scooters; electric golf carts; or power storage systems. However, embodiments are not limited thereto.

As used herein, the term "alkyl" refers to a completely saturated branched or unbranched (or straight-chained or linear) hydrocarbon group. Non-limiting examples of the "alkyl" group are methyl, ethyl, n-propyl, isopropyl, n-butyl, isobutyl, sec-butyl, n-pentyl, isopentyl, neopentyl, n-hexyl, 3-methylhexyl, 2,2-dimethylpentyl, 2,3-dimethylpentyl, and n-heptyl.

At least one hydrogen atom of the alkyl group may be substituted with a halogen atom, a C1-C20 alkyl group substituted with a halogen atom (for example, $CCF_3$, $CHCF_2$, $CH_2F$, $CCl_3$, and the like), a C1-C20 alkoxy group, a C2-C20 alkoxyalkyl group, a hydroxyl group, a nitro group, a cyano group, an amino group, an amidino group, a hydrazine group, a hydrazone group, a carboxyl group or a salt thereof, a sulfonyl group, a sulfamoyl group, a sulfonic acid group or a salt thereof, a phosphoric acid group or a salt thereof, a C1-C20 alkyl group, a C2-C20 alkenyl group, a C2-C20 alkynyl group, a C1-C20 heteroalkyl group, a C6-C20 aryl group, a C7-C20 arylalkyl group, a C6-C20 heteroaryl group, a C6-C20 heteroaryloxy group, a C6-C20 heteroaryloxyalkyl group, or a C6-C20 heteroarylalkyl group.

The term "halogen" refers to fluorine, bromine, chlorine, iodine, or the like.

As used herein, the term "alkoxy" represents "alkyl-O—", wherein the alkyl is the same as described above. Non-limiting examples of the alkoxy group include methoxy, ethoxy, propoxy, 2-propoxy, butoxy, t-butoxy, pentyloxy, and hexyloxy. At least one hydrogen atom of the alkoxy group may be substituted with any of the substituents recited above that may be substituted in place of at least one hydrogen atom of the alkyl group.

As used herein, the term "alkenyl" indicates a branched or unbranched hydrocarbon group with at least one carbon-carbon double bond. Non-limiting examples of the alkenyl group include vinyl, allyl, butenyl, propenyl, and isobutenyl. At least one hydrogen atom in the alkenyl group may be substituted with any of the substituents recited above that may be substituted in place of at least one hydrogen atom of the alkyl group.

As used herein, the term "alkynyl" indicates a branched or unbranched hydrocarbon group with at least one carbon-carbon triple bond. Non-limiting examples of the "alkynyl" group include ethynyl, butynyl, isobutynyl, isopropynyl, and propynyl.

At least one hydrogen atom of the "alkynyl" group may be substituted with any of the substituents recited above that may be substituted in place of at least one hydrogen atom of the alkyl group.

The term "aryl" is construed as including a group with an aromatic ring optionally fused to at least one carbocyclic group. Non-limiting examples of the "aryl" group are phenyl, naphthyl, and tetrahydronaphthyl. At least one hydrogen atom of the "aryl" group may be substituted with any of the substituents for the alkyl group as described above.

The term "arylalkyl" indicates an alkyl group in which one of the hydrogens is substituted with an aryl group. Examples of the arylalkyl group are benzyl groups.

As used herein, the term "aryloxy" indicates "—O-aryl". An example of the aryloxy group is phenoxy. At least one hydrogen atom of the "aryloxy" group may be substituted with any of the substituents recited above that may be substituted in place of at least one hydrogen atom of the alkyl group.

As used herein, the term "heteroaryl group" indicates a monocyclic or bicyclic organic group including at least one heteroatom selected from among nitrogen (N), oxygen (O), phosphorous (P), and sulfur (S), wherein the rest of the cyclic atoms are all carbon. The heteroaryl group may include, for example, one to five heteroatoms, and in an embodiment, may include a five- to ten-membered ring. In the heteroaryl group, S or N may be present in various oxidized forms.

At least one hydrogen atom of the "heteroaryl" group may be substituted with any of the substituents recited above that may be substituted in place of at least one hydrogen atom of the alkyl group.

Non-limiting examples of the heteroaryl group are thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazole-5-yl, tetrazolyl, 2-pyrazine-2-yl, pyrazine-4-yl, pyrazine-5-yl, 2-pyrimidine-2-yl, 4-pyrimidine-2-yl, or 5-pyrimidin-2-yl.

The term "heteroaryl" may indicate a heteroaromatic ring optionally fused to at least one of an aryl group, a cycloaliphatic group, and a heterocyclic group.

The term "heteroarylalkyl" group indicates an alkyl group substituted with a heteroaryl group. At least one hydrogen atom of the heteroarylalkyl group may be substituted with any of the substituents recited above that may be substituted in place of at least one hydrogen atom of the alkyl group.

The term "heteroaryloxy" group indicates a "—O-heteroaryl moiety". At least one hydrogen atom of the heteroaryloxy group may be substituted with any of the substituents that are the same as those recited above in conjunction with the alkyl group.

The term "heteroaryloxyalkyl" group indicates an alkyl group substituted with a heteroaryloxy group. At least one hydrogen atom of the heteroaryloxyalkyl group may be substituted with any of the substituents recited above that may be substituted in place of at least one hydrogen atom of the alkyl group.

As used herein, the term "carbocyclic" group indicates a saturated or partially unsaturated non-aromatic monocyclic, bicyclic, or tricyclic hydrocarbon group.

Non-limiting examples of the monocyclic hydrocarbon group include cyclopentyl, cyclopentenyl, cyclohexyl, and cyclohexenyl. Non-limiting examples of the bicyclic hydrocarbon group include bornyl, decahydronaphthyl, bicyclo[2.1.1]hexyl, bicyclo[2.2.1]heptyl, bicyclo[2.2.1]heptenyl, or bicyclo[2.2.2]octyl.

An example of the tricyclic hydrocarbon group is adamantyl.

At least one hydrogen atom of the "carbocyclic group" may be substituted with any of the substituents recited above that may be substituted in place of at least one hydrogen atom of the alkyl group.

As used herein, the term "heterocyclic group" indicates a five- to ten-membered cyclic hydrocarbon group including at least one heteroatom such as N, S, P, or O. An example of the heterocyclic group is pyridyl. At least one hydrogen atom in the heterocyclic group may be substituted with any of the substituents recited above that may be substituted in place of at least one hydrogen atom of the alkyl group.

The term "sulfonyl" indicates R''—SO$_2$—, wherein R'' is a hydrogen atom, alkyl, aryl, heteroaryl, aryl-alkyl, heteroaryl-alkyl, alkoxy, aryloxy, cycloalkyl, or a heterocyclic group.

The term "sulfamoyl group" refers to H$_2$NS(O$_2$)—, alkyl-NHS(O$_2$)—, (alkyl)$_2$NS(O$_2$)—, aryl-NHS(O$_2$)—, alkyl-(aryl)-NS(O$_2$)—, (aryl)$_2$NS(O)$_2$, heteroaryl-NHS(O$_2$)—, (aryl-alkyl)-NHS(O$_2$)—, or (heteroaryl-alkyl)-NHS(O$_2$)—.

At least one hydrogen atom of the sulfamoyl group may be substituted with any of the substituents recited above that may be substituted in place of at least one hydrogen atom of the alkyl group.

The term "amino group" indicates a group with a nitrogen atom covalently bonded to at least one carbon or heteroatom. "Amino" has the general formula —N(R)$_2$, wherein each R is independently hydrogen, a C1 to C6 alkyl, or a C6 to C12 aryl. The amino group may include, for example, —NH$_2$ and substituted moieties. The term "amino group" also refers to an "alkylamino group" with nitrogen bonded to at least one additional alkyl group, and "arylamino" and "diarylamino" groups with nitrogen bonded to one or two aryl groups, respectively.

One or more embodiments of the present disclosure will now be described in detail with reference to the following examples. However, these examples are only for illustrative purposes and are not intended to limit the scope of the one or more embodiments of the present disclosure.

EXAMPLES

Preparation Example 1

1 wt % of a compound of Formula 3 was added to a nonaqueous organic solvent including a mixture of ethylene carbonate (EC), fluoroethylene carbonate (FEC), ethyl methyl carbonate (EMC), and dimethyl carbonate (DMC) in a volume ratio of 7:7:46:40, to prepare an electrolyte in which 1.15 M LiPF$_6$ was used as a lithium salt.

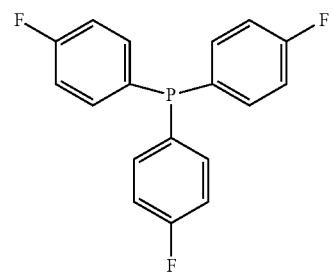

Formula 3

Preparation Example 2

An electrolyte was prepared in the same manner as in Preparation Example 1, except that the amount of the compound of Formula 3 was changed to about 2.9 wt %.

Preparation Example 3

An electrolyte was prepared in the same manner as in Preparation Example 1, except that a compound of Formula 4 was used instead of the compound of Formula 3.

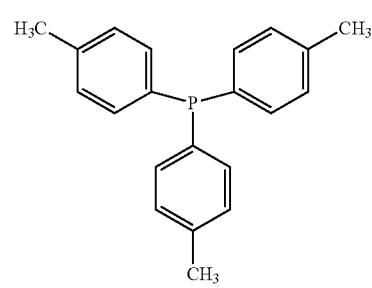

Formula 4

Preparation Example 4

An electrolyte was prepared in the same manner as in Preparation Example 3, except that the amount of Formula 4 was changed to about 2.9 wt %.

Preparation Example 5

An electrolyte was prepared in the same manner as in Preparation Example 1, except that a compound of Formula 5 was used instead of the compound of Formula 3.

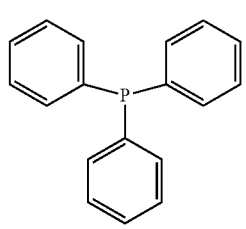

Formula 5

Preparation Example 6

An electrolyte was prepared in the same manner as in Preparation Example 3, except that the amount of Formula 4 was changed to about 0.1 wt %.

Preparation Examples 7 to 11

Electrolytes were prepared in the same manner as in Preparation Example 1, except that the composition of the electrolyte was varied as presented in Table 1.

Preparation Example 12

An electrolyte was prepared in the same manner as in Preparation Example 1, except that vinylene carbonate (VC) and a sultone (methylene methanedisultonate, MMDS) represented by Formula 15 was further added to prepare the electrolyte, the amount of the vinylene carbonate (VC) was 1 wt %, based on a total weight of the electrolyte, and the amount of sultone represented by Formula 15 was about 0.45 wt %, based on a total weight of the electrolyte.

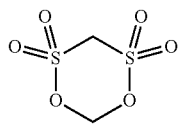

Formula 15

Preparation Example 13

An electrolyte was prepared in the same manner as in Preparation Example 1, except that a mixed solvent of EC, EMC, and DMC in a volume ratio of 20:40:40 was used as the nonaqueous organic solvent to prepare the electrolyte.

Preparation Example 14

An electrolyte was prepared in the same manner as in Preparation Example 1, except that a mixed solvent of EC, FEC, EMC, and DMC in a volume ratio of 17:3:40:40 was used as the non-aqueous organic solvent to prepare the electrolyte, and vinylene carbonate (VC) was further added to prepare the electrolyte, and the amount of the vinylene carbonate (VC) was 1 wt %, based on a total weight of the electrolyte.

Preparation Example 15

An electrolyte was prepared in the same manner as in Preparation Example 7, except that a mixed solvent of EC, FEC, EMC, and DMC in a volume ratio of 7:7:46:40 was used as the non-aqueous organic solvent to prepare the electrolyte, and vinylene carbonate (VC) was further added to prepare the electrolyte, and the amount of the vinylene carbonate (VC) was 1 wt %, based on a total weight of the electrolyte.

The compositions of the electrolytes prepared in Preparation Examples 1 to 14 are presented in Table 1 below.

TABLE 1

| Preparation Example | Amount of additive (wt %) | Solvent (vol. %) | | | | Amount (wt %) | Amount (wt %) |
|---|---|---|---|---|---|---|---|
| | | EC | FEC | EMC | DMC | VC | sultone |
| Preparation Example 1 | Formula 3 1 wt % | 7 | 7 | 46 | 40 | x | x |
| Preparation Example 2 | Formula 3 2.9 wt % | 7 | 7 | 46 | 40 | x | x |
| Preparation Example 3 | Formula 3 1 wt % | 7 | 7 | 46 | 40 | x | x |
| Preparation Example 4 | Formula 4 2.9 wt % | 7 | 7 | 46 | 40 | x | x |
| Preparation Example 5 | Formula 5 1 wt % | 7 | 7 | 46 | 40 | x | x |
| Preparation Example 6 | Formula 4 0.1 wt % | 7 | 7 | 46 | 40 | x | x |
| Preparation Example 7 | Formula 5 1 wt % | 7 | 7 | 46 | 40 | x | x |
| Preparation Example 8 | Formula 5 2.9 wt % | 7 | 7 | 46 | 40 | x | x |
| Preparation Example 9 | Formula 5 0.1 wt % | 7 | 7 | 46 | 40 | x | x |
| Preparation Example 10 | Formula 3 1 wt % | 7 | 7 | 46 | 40 | 1 | x |
| Preparation Example 11 | Formula 4 1 wt % | 7 | 7 | 46 | 40 | 1 | x |
| Preparation Example 12 | Formula 3 1 wt % | 7 | 7 | 46 | 40 | 1 | 0.45 |
| Preparation Example 13 | Formula 3 1 wt % | 20 | x | 40 | 40 | 1 | x |
| Preparation Example 14 | Formula 3 1 wt % | 17 | 3 | 40 | 40 | 1 | X |
| Preparation Example 15 | Formula 5 1 wt % | 7 | 7 | 46 | 40 | 1 | x |

Preparation Examples 16 to 23

Electrolytes were prepared in the same manner as in Preparation Example 1, except that the composition of the electrolyte was varied as represented in Table 2 below. In Table 2, VC denotes vinylene carbonate, and sultone refers to a compound represented by Formula 15.

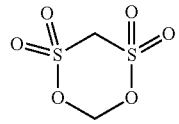

Formula 15

The compositions of the electrolytes prepared in Preparation Examples 16 to 23 are presented in Table 2 below.

Preparation Examples 24 and 25

Electrolytes were prepared in the same manner as in Preparation Example 1, except that the composition of the electrolyte was varied as represented in Table 3 and 4. The compositions of the electrolytes prepared in Preparation Examples 24 and 25 are presented in Tables 3 and 4 below.

TABLE 2

| Preparation Example | Amount of additive (wt %) | Solvent (vol. %) | | | | Amount (wt %) VC | Amount (wt %) sultone |
|---|---|---|---|---|---|---|---|
| | | EC | FEC | EMC | DMC | | |
| Preparation Example 16 | Formula 3 2 wt % | 7 | 7 | 46 | 40 | 1 | 0.5 |
| Preparation Example 17 | Formula 3 2.4 wt % | 7 | 7 | 46 | 40 | 1 | 0.5 |
| Preparation Example 18 | Formula 3 1 wt % MA 1 wt % LiFSI 1 wt % | 7 | 7 | 46 | 40 | 0 | 0.5 |
| Preparation Example 19 | Formula 3 0.5 wt % MA 1 wt % LiFSI 1 wt % | 7 | 7 | 46 | 40 | 0 | 1 |
| Preparation Example 20 | Formula 3 1 wt % | 7 | 7 | 46 | 40 | 0.1 | 0.45 |
| Preparation Example 21 | Formula 3 1 wt % | 7 | 7 | 46 | 40 | 2 | 0.45 |
| Preparation Example 22 | Formula 3 1 wt % | 20 | 0.5 | 42.5 | 37 | 1 | 0.45 |
| Preparation Example 23 | Formula 3 1 wt % | 10 | 10 | 43 | 370 | 1 | 0.45 |

MA: an abbreviation of Maleic anhydride
LiFSI: an abbreviation of lithium bis(fluorosulfonyl)imide

TABLE 3

| Preparation Example | Amount of additive (wt %) | Solvent (vol. %) | | | | Amount (wt %) VC | Amount (wt %) sultone |
|---|---|---|---|---|---|---|---|
| | | EC | FEC | EMC | DMC | | |
| Preparation Example 24 | Formula 3 1 wt % | 20 | 0.5 | 42.5 | 37 | 1 | 0.45 |

TABLE 4

| Preparation Example | Amount of additive (wt %) | Solvent (vol. %) | | | | Amount (wt %) succinic anhydride | Amount (wt %) sultone |
|---|---|---|---|---|---|---|---|
| | | EC | FEC | EMC | DMC | | |
| Preparation Example 25 | Formula 3 1 wt % | 20 | 0.5 | 42.5 | 37 | 1 | 0.45 |

Comparative Preparation Example 1

An electrolyte was prepared in the same manner as in Preparation Example 1, except that the compound of Formula 3 was not used to prepare the electrolyte.

Comparative Preparation Example 2

An electrolyte was prepared in the same manner as in Preparation Example 5, except that the amount of the compound of Formula 5 was changed to 3 wt %.

Comparative Preparation Example 3

An electrolyte was prepared in the same manner as in Comparative Preparation Example 2, except that the compound of Formula 4 was used instead of the compound of Formula 5. In Comparative Preparation Example 3, the amount of the compound of Formula 4 was about 3 wt %.

Comparative Preparation Example 4

An electrolyte was prepared in the same manner as in Preparation Example 1, except that trifluoromethanesulfonyl phosphine (so-called "triflylphosphine") was used instead of the compound of Formula 3.

Comparative Preparation Example 5

An electrolyte was prepared in the same manner as in Comparative Preparation Example 2, except that the compound of Formula 3 was used instead of the compounds of Formula 5. In Comparative Preparation Example 5, the amount of the compound of Formula 3 was about 3 wt %.

The compositions of the electrolytes prepared in Comparative Preparation Examples 1 to 5 are presented in Table 3.

TABLE 3

| Comparative Preparation Example | Amount of additive (wt %) | Solvent (vol. %) | | | | Amount (wt. %) | Amount (wt %) |
|---|---|---|---|---|---|---|---|
| | | EC | FEC | EMC | DMC | VC | sultone |
| Comparative Preparation Example 1 | X | 7 | 7 | 46 | 40 | x | x |
| Comparative Preparation Example 2 | Formula 5 3 wt % | 7 | 7 | 46 | 40 | x | x |
| Comparative Preparation Example 3 | Formula 4 3 wt % | 7 | 7 | 46 | 40 | x | x |
| Comparative Preparation Example 4 | triflylphosphine 1 wt % | 7 | 7 | 46 | 40 | x | x |
| Comparative Preparation Example 5 | Formula 3 3 wt % | 7 | 7 | 46 | 40 | x | x |

Example 1: Manufacture of Lithium Secondary Battery (Full Cell)

Manufacture of Positive Electrode

After $LiNi_{0.6}Co_{0.15}Al_{0.05}O_2$ as a positive active material, denka black as a conducting agent, and polyvinylidene fluoride (PVDF) as a binder were mixed in a weight ratio of 97:1.4:1.6, a N-methylpyrrolidone (NMP) solvent was added thereto to thereby prepare a positive active material slurry with a solid content of about 70%.

The positive active material slurry was coated on both sides of an aluminum foil having a thickness of about 12 μm with a 3-roll coater to a loading level of 37 mg/cm², dried, and then roll-pressed to a density of about 3.6 g/cc, to thereby manufacture a positive electrode.

Manufacture of Negative Electrode

After graphite powder (purity: 99.9% or greater, available from Mitsubishi Chemical Corporation), styrene-butadiene rubber (SBR), and carboxymethyl cellulose (CMC) were mixed together in a weight ratio of 97:1.5:1.5, water was added thereto to obtain a mixture with a solid content of about 70%, and this mixture was uniformly mixed with a PD mixer (available from KM TECH) to thereby prepare a negative active material slurry.

The negative active material slurry was coated on both sides of a copper foil having a thickness of about 10 μm with a 3-roll coater to a loading level of 21.87 mg/cm² dried, and then roll-pressed to a density of about 1.65 g/cc, to thereby manufacture a negative electrode.

Manufacture of Lithium Secondary Battery (Full Cell)

A lithium secondary battery (full cell) was manufactured using the positive electrode and the negative electrode prepared as described above, the electrolyte of Preparation Example 15, and a polyethylene separator.

Example 2

A lithium secondary battery was manufactured in the same manner as in Example 1, except that the electrolyte of Preparation Example 11 was used instead of the electrolyte of Preparation Example 15.

Example 3

A lithium secondary battery was manufactured in the same manner as in Example 1, except that the electrolyte of Preparation Example 11 and $LiNi_{0.8}Co_{0.15}Mn_{0.05}O_2$ as the positive active material were respectively used instead of the electrolyte of Preparation Example 15 and $LiNi_{0.8}Co_{0.15}Al_{0.05}O_2$.

Example 4

A lithium secondary battery was manufactured in the same manner as in Example 1, except that a mixture of SCN1 (Si particles on Graphite, available from BTR) and graphite powder was used instead of the graphite powder during the preparation of the negative electrode. The negative electrode had a capacity of about 430 milliampere hours per gram (mAh/g), a loading level of about 18.75 mg/cm², and a density of about 1.65 g/cc. The amount of SCN1 was about 7.5 parts by weight, based on 100 parts by weight of a total weight of the graphite powder and SCN1.

Example 5

A lithium secondary battery was manufactured in the same manner as in Example 4, except that $LiNi_{0.8}Co_{0.15}Mn_{0.05}O_2$ was used as the positive active material instead of $LiNi_{0.8}Co_{0.15}Al_{0.05}O_2$.

Example 6

A lithium secondary battery was manufactured in the same manner as in Example 5, except that a mixture of SCN2 (available from BTR) and graphite powder was used instead of a mixture of SCN1 and graphite powder. The negative electrode had a capacity of about 430 mAh/g, a loading level of about 18.75 mg/cm$^2$, and a density of about 1.65 g/cc. The amount of SCN2 was about 7.5 parts by weight, based on 100 parts by weight of a total weight of the graphite powder and SCN2.

Example 7

A lithium secondary battery (full cell) was manufactured in the same manner as in Example 1, except that the electrolyte of Preparation Example 14 was used instead of the electrolyte of Preparation Example 15, and the negative electrode of Example 4 (using the mixture of SCN1 and graphite powder) was used instead of the negative electrode of Example 1.

Example 8

A lithium secondary battery was manufactured in the same manner as in Example 1, except that a mixture of graphite powder and silicon oxide (SiO, available from Osaka Titanium Technologies Co., Ltd) was used instead of the graphite powder to prepare the negative electrode. The negative electrode had a capacity of about 430 mAh/g, a loading level of about 18.75 mg/cm$^2$, and a density of about 1.65 g/cc. The amount of silicon oxide (SiO) was about 7.5 parts by weight, based on 100 parts by weight of a total weight of the graphite powder and SiO.

Example 9

A lithium secondary battery was manufactured in the same manner as in Example 1, except that the electrolyte of Preparation Example 14 and $LiNi_{0.8}Co_{0.15}Mn_{0.05}O_2$ as the positive active material were respectively used instead of the electrolyte of Preparation Example 15 and $LiNi_{0.8}Co_{0.15}Al_{0.05}O_2$.

Comparative Example 1

A lithium secondary battery (full cell) was manufactured in the same manner as in Example 1, except that the electrolyte of Comparative Preparation Example 1 was used instead of the electrolyte of Preparation Example 15.

Comparative Example 2

A lithium secondary battery (full cell) was manufactured in the same manner as in Comparative Example 1, except that the negative electrode of Example 4 (using the mixture of the graphite powder and SCN1) was used instead of the negative electrode of Example 1.

Comparative Example 3

A lithium secondary battery (full cell) was manufactured in the same manner as in Comparative Example 1, except that the negative electrode of Example 8 (using the mixture of the graphite powder and SiO) was used instead of the negative electrode of Example 1. The amount of silicon oxide (SiO) was about 7.5 parts by weight, based on 100 parts by weight of a total weight of the graphite powder and SiO.

Comparative Example 4

A lithium secondary battery (full cell) was manufactured in the same manner as in Comparative Example 1, except that the electrolyte of Comparative Preparation Example 4 was used instead of the electrolyte of Comparative Preparation Example 1, and a mixture of the graphite powder and silicon oxide (SiO, available from Osaka Titanium Technologies Co., Ltd) was used instead of graphite powder to prepare the negative electrode. The amount of silicon oxide (SiO) was about 7.5 parts by weight, based on 100 parts by weight of a total weight of the graphite powder and SiO.

Comparative Example 5

A lithium secondary battery was manufactured in the same manner as in Comparative Example 1, except that $LiNi_{0.5}Co_{0.2}Mn_{0.3}O_2$ was used as the positive active material instead of $LiNi_{0.8}Co_{0.15}Al_{0.05}O_2$.

Comparative Example 6

A lithium secondary battery (full cell) was manufactured in the same manner as in Example 1, except that the electrolyte of Comparative Preparation Example 5 was used instead of the electrolyte of Preparation Example 1.

Example 10

A lithium secondary battery was manufactured in the same manner as in Example 1, except that the electrolyte of Preparation Example 12 and $LiNi_{0.85}Co_{0.10}Mn_{0.05}O_2$ as the positive active material were respectively used instead of the electrolyte of Preparation Example 15 and $LiNi_{0.8}Co_{0.15}Al_{0.05}O_2$.

Example 11

A lithium secondary battery was manufactured in the same manner as in Example 10, except that $LiNi_{0.88}Co_{0.8}Mn_{0.4}O_2$ was used as the positive active material instead of $LiNi_{0.85}Co_{0.10}Mn_{0.05}O_2$.

Example 12

A lithium secondary battery was manufactured in the same manner as in Example 10, except that the electrolyte of Preparation Example 13 was used instead of the electrolyte of Preparation Example 12.

Example 13

A lithium secondary battery was manufactured in the same manner as in Example 10, except that the electrolyte of Preparation Example 14 was used instead of the electrolyte of Preparation Example 12.

Example 14

A lithium secondary battery was manufactured in the same manner as in Example 10, except that the electrolyte of Preparation Example 16 was used instead of the electrolyte of Preparation Example 12.

Example 15

A lithium secondary battery was manufactured in the same manner as in Example 10, except that the electrolyte of Preparation Example 17 was used instead of the electrolyte of Preparation Example 12.

Example 16

A lithium secondary battery was manufactured in the same manner as in Example 11, except that the electrolyte of Preparation Example 18 was used instead of the electrolyte of Preparation Example 12, and the negative electrode of Example 6 (using a mixture of graphite powder and SCN2) was used instead of the negative electrode of Example 1. The amount of SCN2 was about 7.5 parts by weight, based on 100 parts by weight of a total weight of the graphite powder and SCN2.

Example 17

A lithium secondary battery was manufactured in the same manner as in Example 11, except that the electrolyte of Preparation Example 19 was used instead of the electrolyte of Preparation Example 12, and the negative electrode of Example 6 (using a mixture of graphite powder and SCN2) was used instead of the negative electrode of Example 1. The amount of SCN2 was about 7.5 parts by weight, based on 100 parts by weight of a total weight of the graphite powder and SCN2.

Example 18

A lithium secondary battery was manufactured in the same manner as in Example 10, except that $LiNi_{0.88}Co_{0.8}Mn_{0.04}O_2$ was used as the positive active material instead of $LiNi_{0.85}Co_{0.10}Mn_{0.05}O_2$, and the electrolyte of Preparation Example 20 was used instead of the electrolyte of Preparation Example 12.

Example 19

A lithium secondary battery was manufactured in the same manner as in Example 10, except that $LiNi_{0.88}Co_{0.8}Mn_{0.04}O_2$ was used as the positive active material instead of $LiNi_{0.85}Co_{0.10}Mn_{0.05}O_2$, and the electrolyte of Preparation Example 21 was used instead of the electrolyte of Preparation Example 12.

Example 20

A lithium secondary battery was manufactured in the same manner as in Example 11, except that the electrolyte of Preparation Example 22 was used instead of the electrolyte of Preparation Example 12, and the negative electrode of Example 6 (using the mixture of the graphite powder and SCN2) was used instead of the negative electrode of Example 1. The amount of SCN2 was about 7.5 parts by weight, based on 100 parts by weight of a total weight of the graphite powder and SCN2.

Example 21

A lithium secondary battery was manufactured in the same manner as in Example 11, except that the electrolyte of Preparation Example 23 was used instead of the electrolyte of Preparation Example 12, and the negative electrode of Example 6 was used instead of the negative electrode of Example 1.

Evaluation Example 1: High-Temperature Charge-Discharge Characteristics (Lifespan and DCIR)

1) Examples 1 to 9 and Comparative Examples 1 to 6

Each of the lithium secondary batteries of Examples 1 to 9 and Comparative Examples 1 to 6 was charged at 45° C. with a constant current at a 0.1 Coulomb (C) rate to a voltage of about 4.30 V and then with a constant voltage of 4.30 V until a cutoff current at a 0.01 C rate, and then discharged with a constant current at a 0.1 C rate to a voltage of about 2.8 V (Formation process, 1$^{st}$ cycle). This charging and discharging process was performed twice further to complete the formation process.

After the formation process, each of the lithium secondary batteries was charged and discharged at a high temperature (45° C.) with a constant current at 1 C in a voltage range of about 2.8 V to 4.3 V. The cutoff current in a CC-CV mode was 0.01 C.

This charging and discharging process was repeated 300 times.

Lifespan characteristics and direct current internal resistance (DCIR) characteristics of the lithium secondary batteries at 45° C. were evaluated. The results are shown in Table 4. A lifespan of each of the lithium secondary batteries was calculated using Equation 1.

Lifespan (%)=(Discharge capacity after 300$^{th}$ cycle/ Discharge capacity after 1$^{st}$ cycle)×100   Equation 1

A percentage increase in DCIR was calculated using Equation 2.

DCIR increase (%)=(DCIR of battery after 300$^{th}$ cycle/DCIR of battery after 1$^{st}$ cycle)×100   Equation 2

TABLE 4

| Example | Lifespan (%) | DCIR increase (%) |
| --- | --- | --- |
| Example 1 | 83 | 148 |
| Example 2 | 84 | 132 |
| Example 3 | 87 | 130 |
| Example 4 | 74 | 158 |
| Example 5 | 76 | 144 |
| Example 6 | 78 | 142 |
| Example 7 | 76 | 158 |
| Example 8 | 74 | 156 |
| Example 9 | 86 | 142 |
| Comparative Example 1 | 78 | 193 |
| Comparative Example 2 | 69 | 205 |
| Comparative Example 3 | 68 | 190 |
| Comparative Example 4 | 57 | 230 |
| Comparative Example 5 | 72 | 220 |
| Comparative Example 6 | 72 | 210 |

Referring to Table 4, the lithium secondary batteries of Examples 1 to 9 were found to have improved lifespan characteristics at 45° C., as compared with the lithium secondary batteries of Comparative Examples 1 to 6. Referring to Table 4, the lithium secondary batteries of Examples 1 to 9 were found to have a reduced increase in DCIR at 45° C., as compared with the lithium secondary batteries of Comparative Examples 1 to 6.

2) Examples 10 to 21, 23, 24 and Comparative Example 8

Lifespan characteristics and direct current internal resistance (DCIR) characteristics of lithium secondary batteries of E10 to 21, 23, 24 and Comparative Example 8 were at 45° C. were evaluated in the same manner as in Examples 1 to 9 and Comparative Examples 1 to 6. The results are shown in Table 5.

TABLE 5

| Example | Lifespan (%) | DCIR increase (%) |
|---|---|---|
| Example 10 | 87 | 116 |
| Example 11 | 86 | 118 |
| Example 12 | 86 | 147 |
| Example 13 | 87 | 146 |
| Example 14 | 86 | 115 |
| Example 15 | 86 | 126 |
| Comparative Example 8 | 71 | 158 |
| Example 16 | 83 | 116 |
| Example 17 | 83 | 112 |
| Example 18 | 83 | 125 |
| Example 19 | 85 | 122 |
| Example 20 | 81 | 119 |
| Example 21 | 83 | 126 |
| Example 23 | 81 | 135 |
| Example 24 | 83 | 138 |

Referring to Table 5, the lithium secondary batteries of Examples 10 to 21, 23, 24 were found to have improved lifespan characteristics at 45° C., as compared with the lithium secondary batteries of Comparative Example 8. Also, the lithium secondary batteries of Examples 10 to 21, 23, 24 were found to have a reduced increase in DCIR at 45° C., as compared with the lithium secondary batteries of Comparative Example 8.

Evaluation Example 2: Initial Discharge Capacity

Each of the lithium secondary batteries of Example 1, Comparative Example 1, and Comparative Example 5 was charged at room temperature (25° C.) with a constant current at a 0.2 C rate to a voltage of 4.3 V, then with a constant voltage of 4.3 V to a current at 0.01 C, and then discharged with a constant current at a 0.2 C rate to a voltage of 2.8 V ($1^{st}$ cycle). An initial discharge capacity of each of the lithium secondary batteries was evaluated. The results are shown in Table 6.

TABLE 6

| Example | Initial capacity (mAh) |
|---|---|
| Example 1 | 503 |
| Comparative Example 1 | 498 |
| Comparative Example 5 | 330 |

Referring to Table 6, the lithium secondary battery of Example 1 was found to have an improved initial discharge capacity, as compared with the lithium secondary batteries of Comparative Examples 1 and 5.

As described above, according to an embodiment, an electrolyte for a lithium secondary battery may include a compound represented by Formula 1, and a lithium secondary battery using the electrolyte may have improved capacity and lifespan characteristics.

It should be understood that embodiments described herein should be considered in a descriptive sense only and not for purposes of limitation. Descriptions of features or aspects within each embodiment should be considered as available for other similar features or aspects in another embodiment.

While one or more embodiments have been described with reference to the FIGURES, it will be understood by those of ordinary skill in the art that various changes in form and details may be made therein without departing from the spirit and scope as defined by the following claims.

What is claimed is:

1. An electrolyte for a lithium secondary battery, the electrolyte comprising:
a compound represented by Formula 1;
a lithium salt; and
an organic solvent,
wherein an amount of the compound represented by Formula 1 is about 0.1 weight percent to about 3.0 weight percent, based on a total weight of the electrolyte, and wherein the electrolyte further comprises a disultone compound represented by Formula 7:

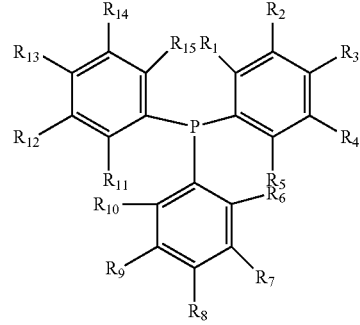

Formula 1 wherein, in Formula 1, $R_1$ to $R_{15}$ are each independently hydrogen, fluorine, a substituted or unsubstituted C1-C10 alkyl group, a substituted or unsubstituted C6-C10 aryl group, or a combination thereof,
wherein when at least one of $R_1$ to $R_{15}$ is hydrogen, at least one of $R_1$ to $R_{15}$ is fluorine, a substituted or unsubstituted C1-C10 alkyl group, or a substituted or unsubstituted C6-C10 aryl group, and
wherein when at least one of $R_1$ to $R_{15}$ is fluorine, at least one of $R_1$ to $R_{15}$ is hydrogen, a substituted or unsubstituted C1-C10 alkyl group, or a substituted or unsubstituted C6-C10 aryl group,

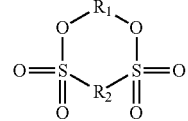

Formula 7 wherein, in Formula 7,
$R_1$ and $R_2$ are each independently a substituted C1-C30 alkylene group or an unsubstituted C1-C30 alkylene group, and
a substituent of the substituted C1-C30 alkylene group is at least one of a halogen, a methyl group, an ethyl group, an n-proply group, an isopropyl group, a n-butyl group, a sec-butyl group, a tert-butyl group, a vinyl group, a propinyl group, a butynyl group, a propenyl group, or a butenyl group.

2. The electrolyte of claim 1, wherein the amount of the compound represented by Formula 1 is about 0.1 weight percent to about 2.9 weight percent, based on the total weight of the electrolyte.

3. The electrolyte of claim 1, wherein the compound represented by Formula 1 is a compound represented by Formula 2:

Formula 2

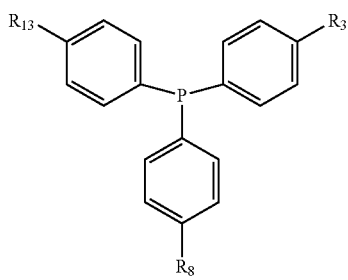

wherein, in Formula 2, $R_3$, $R_8$, and $R_{13}$ are each independently selected from hydrogen, fluorine, and a methyl group.

4. The electrolyte of claim 1, wherein the compound represented by Formula 1 is a compound represented by at least one of Formula 3, Formula 4, Formular 5, Formula 6, Formula 6a, or Formula 6b:

Formula 3

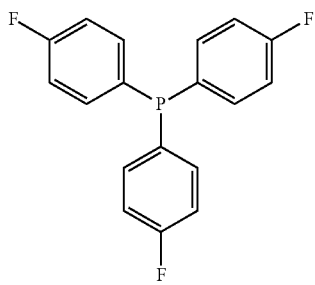

Formula 4

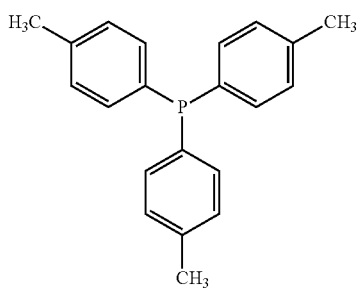

Formula 5

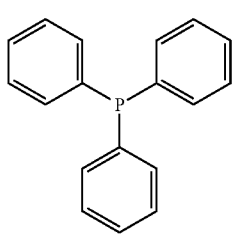

Formula 6

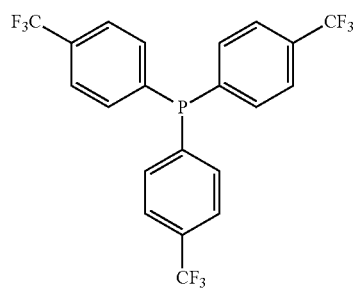

Formula 6a

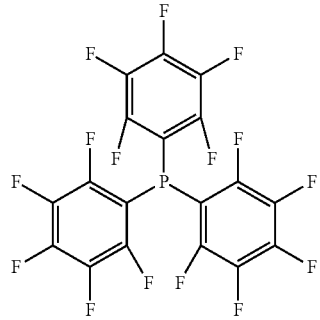

Formula 6b

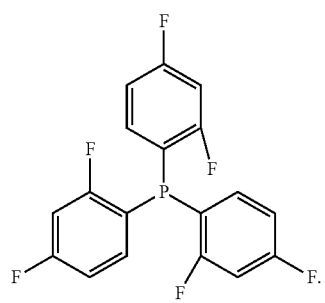

5. The electrolyte of claim 1, wherein the disultone compound represented by Formula 7 is a disultone compound represented by Formula 7a-1 to 7a-4, and an total amount of the disultone compound represented by Formula 7a-1 to 7a-4 is about 0.5 weight percent to about 2 weight percent, based on the total weight of the electrolyte:

Formula 7a 7a-1

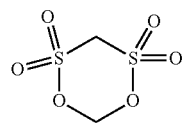

7a-2

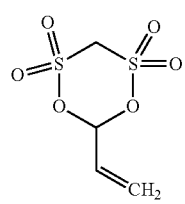

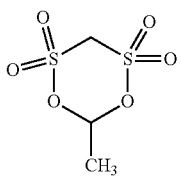

7a-3

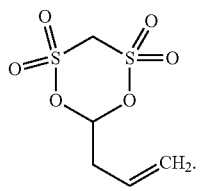

7a-4

6. The electrolyte of claim 1, wherein a concentration of the lithium salt is about 0.1 moles per liter to about 5.0 moles per liter.

7. The electrolyte of claim 6, wherein the lithium salt is at least one of $LiPF_6$, $LiBF_4$, $LiCF_3SO_3$, $Li(CF_3SO_2)_2N$, $LiC_4F_9SO_3$, $Li(FSO_2)_2N$, $LiN(SO_2CF_2CF_3)_2$, a compound represented by Formula 8, a compound represented by Formula 9, a compound represented by Formula 10, or a compound represented by Formula 11:

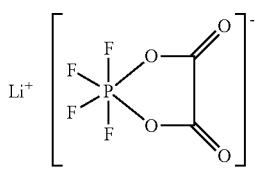

Formula 8

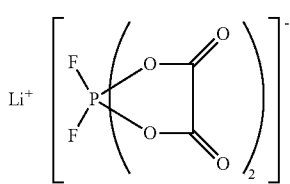

Formula 9

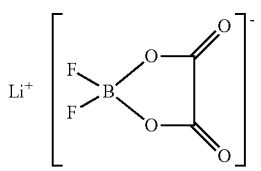

Formula 10

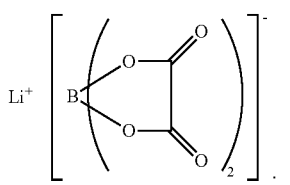

Formula 11

8. The electrolyte of claim 6, wherein
the lithium salt is at least of $LiPF_6$, $Li(FSO_2)_2N$, or a compound represented by Formula 11, and
the concentration of the lithium salt is about 0.8 moles per liter to about 2 moles per liter:

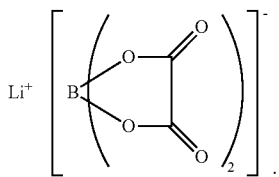

Formula 11

9. A lithium secondary battery comprising:
a positive electrode;
a negative electrode; and
the electrolyte of claim 1, disposed between the positive electrode and the negative electrode.

10. The lithium secondary battery of claim 9, wherein the positive electrode comprises a nickel-rich lithium-nickel composite oxide containing about 70 mole percent to about 95 mole percent of nickel, based on a total molar amount of transition metals in the nickel-rich lithium-nickel composite oxide.

11. The lithium secondary battery of claim 10, wherein the nickel-rich lithium-nickel composite oxide is a compound represented by Formula 14:

$$Li_aNi_xCo_yMn_zM_cO_{2-b}A_b$$ Formula 14 wherein, in Formula 14,
M is at least one of vanadium, magnesium, gallium, silicon, tungsten, molybdenum, iron, chromium, copper, zinc, titanium, aluminum, and boron,
A is at least one of F, S, Cl, or Br, and
$1.0 \leq a \leq 1.2$, $0.7 \leq x<1$, $0 \leq y<1$, $0 \leq z<1$, $0 \leq c<1$, $x+y+z+c=1$, and $0 \leq b \leq 0.2$.

12. The lithium secondary battery of claim 11, wherein the nickel-rich lithium-nickel composite oxide is a compound represented by Formula 14a or Formula 14b:

$$LiNi_xCo_yMn_zO_2$$ Formula 14a $$LiNi_xCo_yAl_zO_2$$ Formula 14b wherein, in Formula 14a and Formula 14b,
$0.8 \leq x \leq 0.95$, $0<y \leq 0.2$, and $0<z \leq 0.1$.

13. The lithium secondary battery of claim 9, wherein the negative electrode comprises at least one of a silicon compound, a carbonaceous material, a composite of a silicon compound and a carbonaceous material, and a silicon oxide of the formula $SiO_x$, wherein $0<x<2$.

14. The lithium secondary battery of claim 9, wherein a direct current internal resistance of the lithium secondary battery after 300 cycles of charging and discharging is about 165% to about 112% than a direct current internal resistance of the lithium secondary battery after 1 cycle of charging and discharging, as measured at about 45° C.

15. A lithium secondary battery comprising:
a positive electrode comprising a nickel-rich lithium-nickel composite oxide containing about 70 mole percent to about 95 mole percent of nickel, based on a total molar amount of transition metals in the nickel-rich lithium-nickel composite oxide;
a negative electrode; and
an electrolyte disposed between the positive electrode and the negative electrode, the electrolyte comprising
a lithium salt,
an organic solvent,
a compound represented by Formula 1, wherein an amount of the compound represented by Formula 1 is about 0.1 weight percent to less than about 3 weight percent, based on a total weight of the electrolyte, and
wherein the electrolyte further comprises a disultone compound represented by Formula 7:

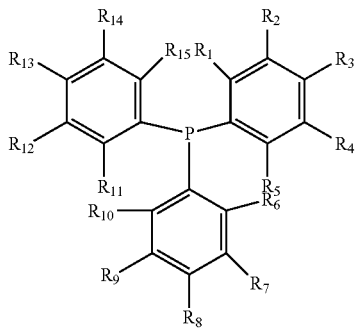

Formula 1 wherein, in Formula 1, $R_1$ to $R_{15}$ are each independently hydrogen, fluorine, a substituted or unsubtituted C1-C10 alkyl group, or a substituted or unsubstituted C6-C10 aryl group,

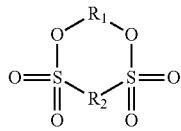

Formula 7 wherein, in Formula 7,
$R_1$ and $R_2$ are each independently a substituted C1-C30 alkylene group or an unsubstituted C1-C30 alkylene group, and
a substituent of the substituted C1-C30 alkylene group is at least one of a halogen, a methyl group, an ethyl group, an n-proply group, an isopropyl group, a n-butyl group, a sec-butyl group, a tert-butyl group, a vinyl group, a propinyl group, a butynyl group, a propenyl group, or a butenyl group.

16. The lithium secondary battery of claim 15, wherein the nickel-rich lithium-nickel composite oxide is a compound represented by Formula 14:

Formula 14 wherein, in Formula 14,
M is at least one of vanadium, magnesium, gallium, silicon, tungsten, molybdenum, iron, chromium, copper, zinc, titanium, aluminum, or boron,
A is at least one of F, S, Cl, or Br, and $1.0 \leq a \leq 1.2$, $0.7 \leq x < 1$, $0 < y < 1$, $0 \leq z < 1$, $0 \leq c < 1$, $x+y+z+c=1$, and $0 \leq b \leq 0.2$.

17. An electrolyte for a lithium secondary battery, the electrolyte comprising:
a compound represented by Formula 1;
a lithium salt; and
an organic solvent,
wherein an amount of the compound represented by Formula 1 is about 0.1 weight percent to about 3.0 weight percent, based on a total weight of the electrolyte, and wherein the electrolyte further comprises a disultone compound represented by Formula 7:

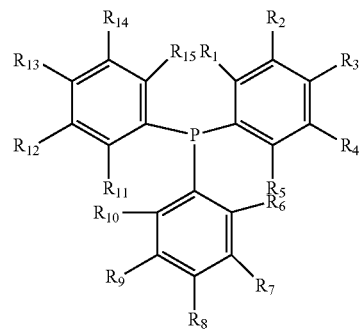

Formula 1 wherein, in Formula 1, $R_1$ to $R_{15}$ are each independently hydrogen, fluorine, a substituted or unsubstituted C1-C10 alkyl group, or a substituted or unsubstituted C6-C10 aryl group, or a combination thereof.
wherein when at least one of $R_1$ to $R_{15}$ is hydrogen, at least one of $R_1$ to $R_{15}$ is fluorine, a substituted or unsubstituted C1-C10 alkyl group, or a substituted or unsubstituted C6-C10 aryl group, and
wherein when at least one of $R_1$ to $R_{15}$ is fluorine, at least one of $R_1$ to $R_{15}$ is hydrogen, a substituted or unsubstituted C1-C10 alkyl group, or a substituted or unsubstituted C6-C10 aryl group,

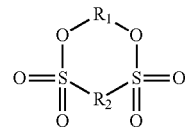

Formula 7 wherein, in Formula 7,
$R_1$ and $R_2$ are each independently a substituted C1-C30 alkylene group or an unsubstituted C1-C30 alkylene group, and
a substituent of the substituted C1-C30 alkylene group is at least one of a halogen, a methyl group, an ethyl group, an n-propyl group, an isopropyl group, a n-butyl group, a sec-butyl group, a tert-butyl group, a vinyl group, a propinyl group, a butynyl group, a propenyl group, or a butenyl group.

18. The lithium secondary battery of claim 17, wherein the compound represented by Formula 1 is a compound represented by at least one of Formula 3, Formula 4, Formula 6, or Formula 6b:

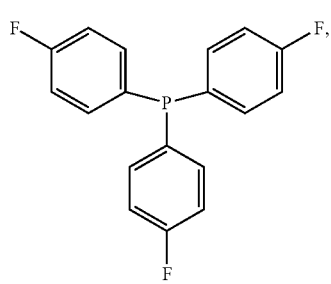

Formula 3

Formula 4
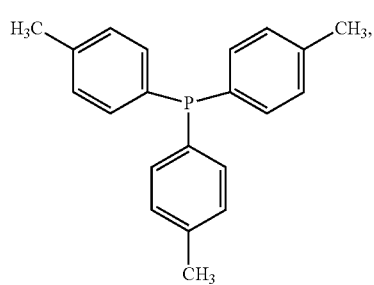
Formula 6
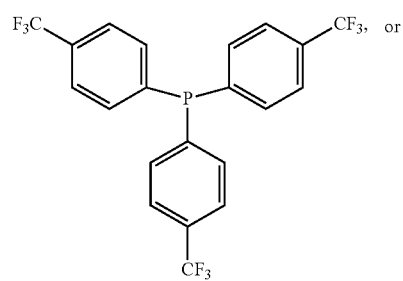
Formula 6b
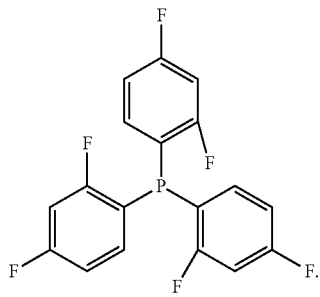
* * * * *